United States Patent [19]
Lauterjung

[11] Patent Number: 5,707,388
[45] Date of Patent: Jan. 13, 1998

[54] HIGH HOOP STRENGTH INTRALUMINAL STENT

[75] Inventor: Karl L. Lauterjung, Munich, Germany

[73] Assignee: InterVascular, Inc., Clearwater, Fla.

[21] Appl. No.: 790,841

[22] Filed: Jan. 30, 1997

Related U.S. Application Data

[62] Division of Ser. No. 353,066, Dec. 9, 1994, Pat. No. 5,630,829.

[51] Int. Cl.$^6$ .............................. A61M 29/00; A61F 2/06
[52] U.S. Cl. .............................. 606/198; 623/1; 623/12
[58] Field of Search ........................... 623/1, 12; 604/96; 606/191–195, 198

[56] References Cited

U.S. PATENT DOCUMENTS

| | | |
|---|---|---|
| 4,214,587 | 7/1980 | Sakura, Jr. . |
| 4,512,338 | 4/1985 | Balko et al. . |
| 4,550,447 | 11/1985 | Seiler, Jr. et al. . |
| 4,655,771 | 4/1987 | Wallsten . |
| 4,739,762 | 4/1988 | Palmaz . |
| 4,776,337 | 10/1988 | Palmaz . |
| 4,830,003 | 5/1989 | Wolff et al. . |
| 4,856,516 | 8/1989 | Hillstead . |
| 5,019,090 | 5/1991 | Pinchuk . |
| 5,064,435 | 11/1991 | Porter . |
| 5,116,365 | 5/1992 | Hillstead . |
| 5,123,917 | 6/1992 | Lee . |
| 5,133,732 | 7/1992 | Wiktor . |
| 5,135,536 | 8/1992 | Hillstead . |
| 5,139,480 | 8/1992 | Hickle et al. . |
| 5,171,252 | 12/1992 | Friedland . |
| 5,171,262 | 12/1992 | MacGregor . |
| 5,197,978 | 3/1993 | Hess . |
| 5,217,483 | 6/1993 | Tower . |
| 5,226,913 | 7/1993 | Pinchuk . |
| 5,234,447 | 8/1993 | Kaster et al. . |
| 5,282,823 | 2/1994 | Schwartz et al. . |
| 5,282,824 | 2/1994 | Gianturco . |
| 5,290,305 | 3/1994 | Inoue . |
| 5,292,331 | 3/1994 | Boneau . |
| 5,304,200 | 4/1994 | Spaulding . |
| 5,314,472 | 5/1994 | Fontaine . |
| 5,397,355 | 3/1995 | Marin et al. . |

FOREIGN PATENT DOCUMENTS

| | | |
|---|---|---|
| WO 93/13824 | 7/1993 | WIPO . |
| WO 93/19804 | 10/1993 | WIPO . |
| WO 94/03127 | 2/1994 | WIPO . |

*Primary Examiner*—Nancy Mulcare
*Attorney, Agent, or Firm*—Lerner, David, Littenberg, Krumholz & Mentlik

[57] ABSTRACT

An intraluminal stent is constructed to provide improved hoop strength over conventional stents. The stent includes a plurality of elongated members extending in a circumferential direction around an axis and curving in two opposite directions transverse to the circumferential direction. Each of the elongated members is curved over substantially its entire extent, preferably so that the curved portions define an arc of a circle. The elongated members are joined to one another at cusps pointing in opposite axial directions. The cusps are movable in opposite axial directions between an expanded condition in which the opposed cusps are relatively close to one another and the elongated members define an expanded circumference, and a collapsed condition in which the opposed cusps are relatively distant to one another and the elongated members define a collapsed circumference which is smaller than the expanded circumference. The stent may be formed as a single loop or as a plurality of loops extending in an axial direction.

8 Claims, 6 Drawing Sheets

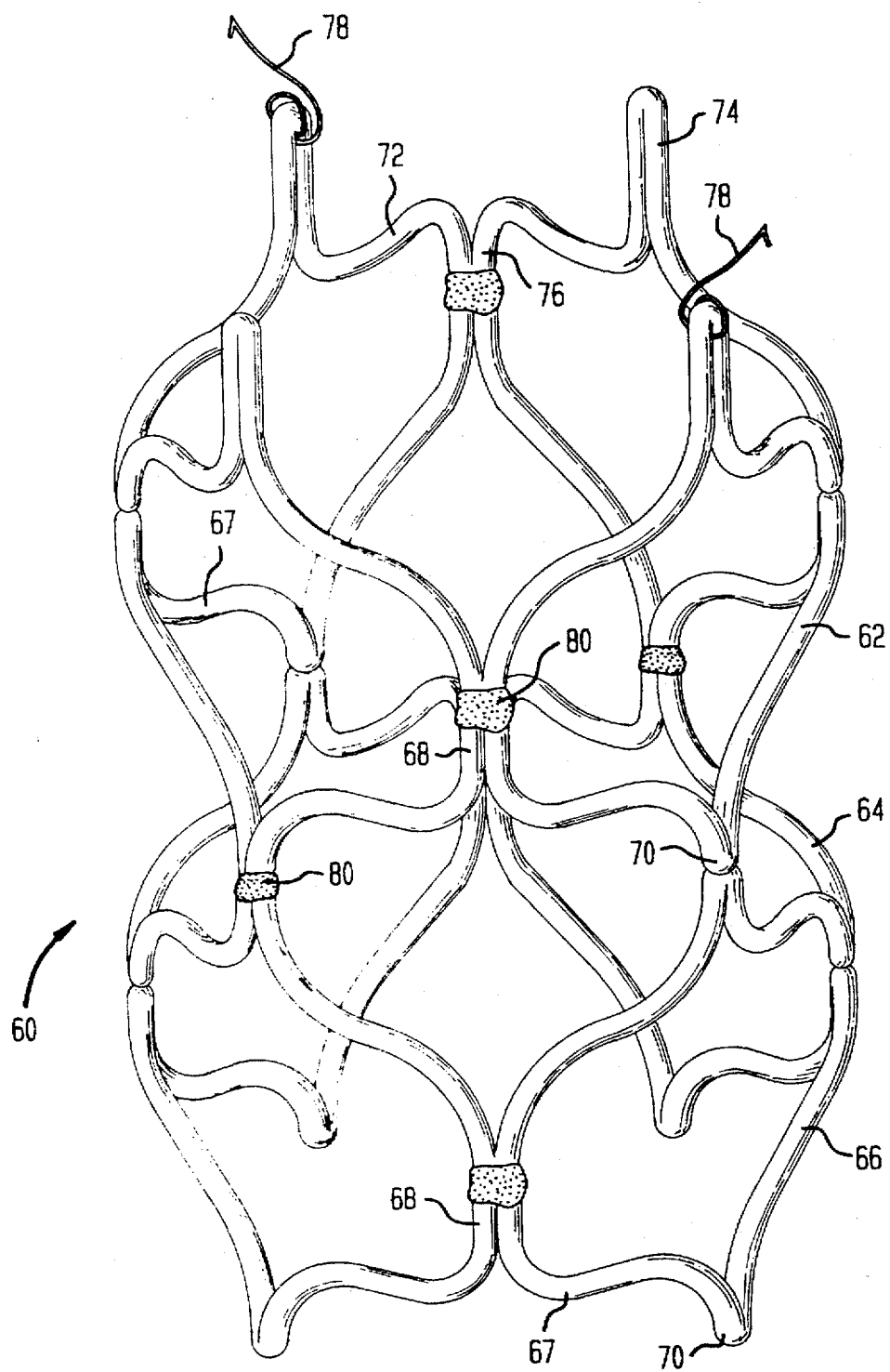

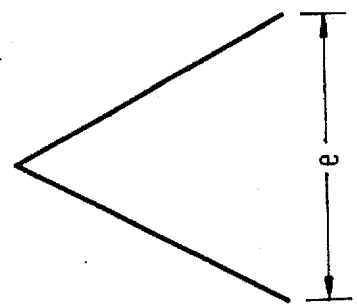
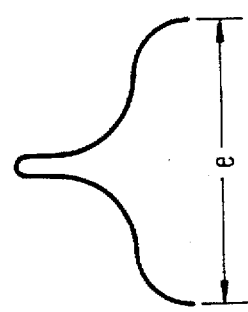
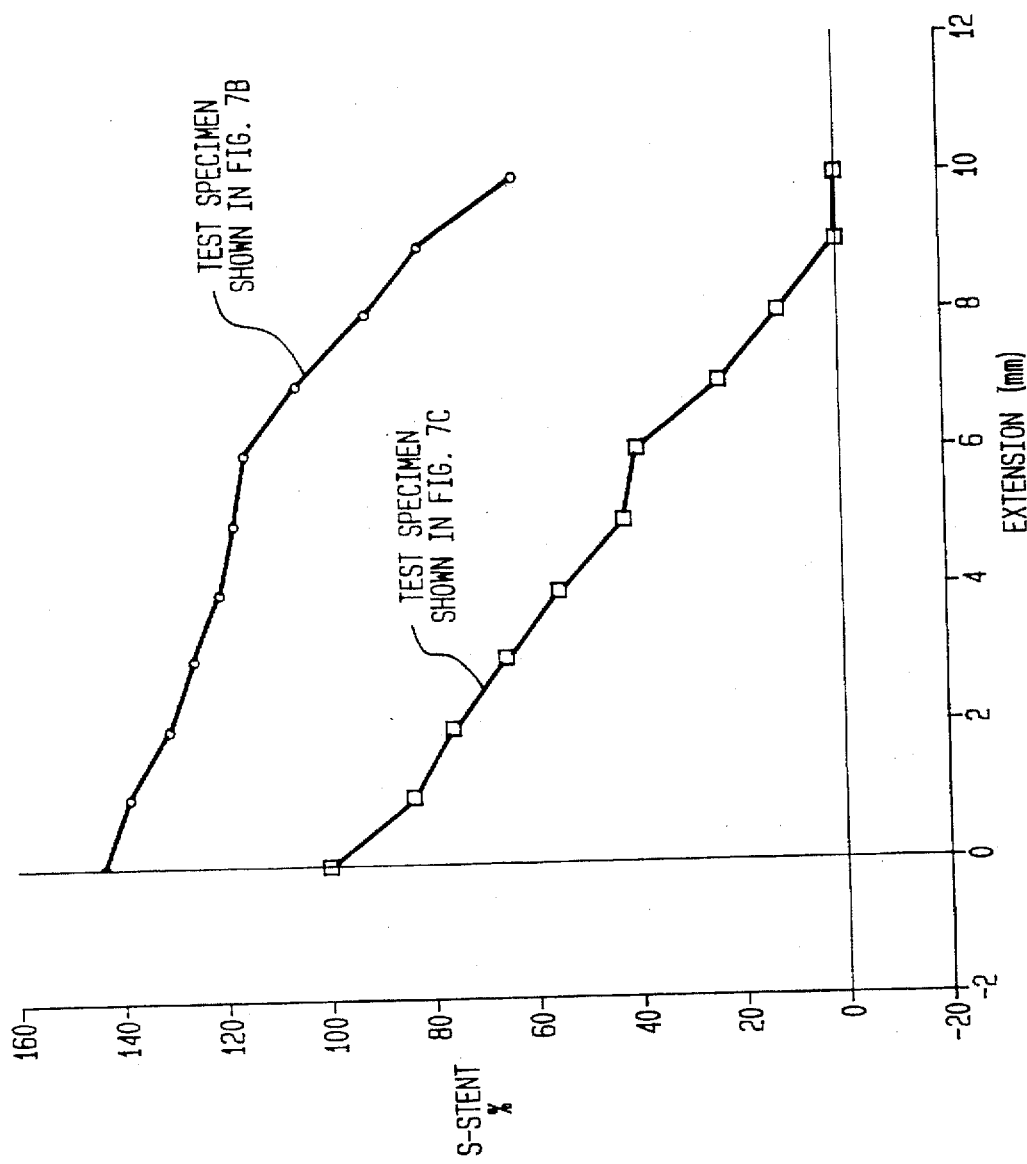

HIGH HOOP STRENGTH INTRALUMINAL STENT

This is a division, of application Ser. No. 08/353,066 filed Dec. 9, 1994, which is now U.S. Pat. No. 5,630,829.

FIELD OF THE INVENTION

The present invention relates generally to prosthetic devices for use within a body passageway or duct and, more particularly, to an intraluminal stent for repairing blood vessels. Still more particularly, the present invention relates to intraluminal stents having high hoop strength.

BACKGROUND OF THE INVENTION

As its name implies, intraluminal stents are devices which are implantable within a body lumen for treating abnormal conditions within the lumen. For example, these devices have found use in maintaining the patency of collapsing and partially occluded blood vessels, particularly to prevent acute closure and restenosis after a vessel has been enlarged by a percutaneous transluminal coronary angioplasty procedure. These devices have also been used to reinforce other body lumens, such as the urinary tract, the bile tract, the intestinal tract and the like. They have found further use as fixation devices for holding intraluminal prosthetic grafts open and in place in the repair of weakened or abnormally dilated portions of a blood vessel.

Conventional stents are formed from a wire or the like which has been bent back and forth in a generally zig-zag pattern in a longitudinal direction and then wound in a circumferential direction transverse to the longitudinal direction to form one or more loops of a predetermined circumference. Typically, the stent is radially expandable from a collapsed condition in which the circumference of the stent is minimized so that the stent can be delivered intraluminally, to an expanded condition in which the circumference of the stent approaches the predetermined circumference to support and reinforce the lumen. The stent is normally held in the collapsed condition by a catheter during intraluminal delivery to the repair site. Once properly located, the stent is removed from the catheter and radially expanded until its circumference firmly contacts the interior wall of the lumen to hold the stent in this implanted location. This radial expansion of the stent may be effected by the dilation of an angioplasty balloon placed axially within the stent. Alternatively, the stent may be made from a shape memory metal, whereby the stent will automatically assume its expanded circumference as its temperature increases upon implantation at the desired location.

Regardless of the mechanism by which the stent is placed in its expanded condition, an important attribute of the stent is its ability to provide radial support. This capability is a concern not only where the stent is being used to maintain the patency of the lumen in which it is located, but also where the stent is being used in conjunction with a prosthetic graft to keep the graft open and to hold it at the location at which it was implanted. The ability of the stent to provide this radial support, particularly over long periods of time, is directly related to the hoop strength which the stent exhibits. For conventional stents having a generally zig-zag configuration, the hoop strength depends primarily upon the number of bends along the circumference of the stent, the elastic properties of the wire from which the stent is formed, and the diameter of the wire. Currently available stents generally have a sufficient hoop strength for use in small caliber vessels and the like because they require a relatively small number of bends along their circumference. However, where the stents have a larger circumference for use in larger caliber vessels, such as the aorta, they include a much larger number of bends and thus exhibit a lower hoop strength which is generally insufficient to maintain the patency of these larger lumens and to fix larger circumference grafts in place therein. A simple approach to increasing the hoop strength of these stents without changing the material from which they are formed is to form the stent from a larger diameter wire. Although this approach may produce satisfactory hoop strengths, it has the negative affect of increasing the bulk of the stent and thus contributes to delivery problems.

There therefore exists a need for a stent having sufficient hoop strength to provide long term radial support and graft fixation in large caliber arteries and other body lumens. More particularly, there exists a need for a stent which exhibits this high hoop strength with little to no increase in bulk over conventional stents and which therefore does not contribute to difficulties in intraluminal delivery.

SUMMARY OF THE INVENTION

The present invention addresses these needs.

In stents having a conventional shape with straight legs joined to one another at acute angle bends in a zig-zag pattern, the bends generate substantially the entire hoop strength of the stent. That is, upon the application of forces to a stent in a radially inward direction, the total collapse of the stent will be resisted by the resistance of the bends to further bending. Hence, the straight legs which comprise the predominant portion of the stent contribute little to the hoop strength. In accordance with the present invention, the hoop strength of a stent has now been significantly increased by replacing the straight legs with legs which are smoothly curved along substantially their entire length and which therefore contribute to the overall hoop strength of the stent.

Thus, one aspect of the present invention provides an intraluminal stent having improved hoop strength. One embodiment of a stent in accordance with this aspect of the present invention includes a plurality of elongated members extending in a circumferential direction around an axis and curving in two opposite directions transverse to the circumferential direction. Each of the elongated members is curved over substantially its entire extent, the members being joined to one another at cusps pointing in directions transverse to the circumferential direction. In preferred embodiments, the cusps point in opposed axial directions, the cusps pointing in one axial direction having an axial length which is greater than the cusps pointing in the other axial direction. A barb may be connected to one or more of the cusps, preferably the longer cusps.

The elongated members together may define a loop which is foldable between a collapsed circumference and an expanded circumference greater than the collapsed circumference. Each of the elongated members preferably includes a first portion curving in a first direction and a second portion curving in a second direction opposite to the first direction. More preferably, each of the first and second portions of the elongated members define an arc having a constant radius of curvature and a length described by an angle of between about 30 degrees and about 180 degrees. In highly preferred embodiments, the arcs have a length described by an angle of about 90 degrees. Stents in accordance with this aspect of the present invention desirably are formed from a shape-memory material.

Another embodiment of a stent in accordance with this aspect of the present invention includes a plurality of elongated members extending in a circumferential direction around an axis and curving in two opposite directions transverse to the circumferential direction, the elongated members being joined to one another at cusps pointing in opposed axial directions. The cusps are movable in the opposed axial directions between an expanded condition and a collapsed condition. In the expanded condition, the cusps pointing in one axial direction are spaced from the cusps pointing in the other axial direction by a predetermined distance and the elongated members define an expanded circumference. In the collapsed condition, the cusps pointing in the one axial direction are spaced from the cusps pointing in the other axial direction by a distance greater than the predetermined distance and the elongated members define a collapsed circumference smaller than the expanded circumference. In accordance with this embodiment, movement of the cusps from the expanded condition to the collapsed condition substantially straightens the elongated members without plasticly deforming same.

In yet another embodiment of the present invention, an intraluminal stent includes a plurality of loops extending in a circumferential direction around an axis at spaced distances along the axis between a first end and a second end, each of the loops including a plurality of elongated members curving in two opposite directions transverse to the circumferential direction. Each of the elongated members is curved over substantially its entire extent, the members being joined to one another at cusps pointing in directions transverse to the circumferential direction.

In one variant hereof, the cusps in each of the loops point in opposed axial directions, each loop including at least one cusp pointing in one axial direction connected to at least one cusp pointing in the other axial direction in an adjacent loop.

In another variant hereof, each of the loops has a first end and a second end, the loops being connected to one another with the second end of one of the loops connected to the first end of an adjacent loop so that the loops define a continuous helix extending in the axial direction.

In still another embodiment of the present invention, an intraluminal stent includes a plurality of loops extending in a circumferential direction around an axis at spaced distances along the axis, each of the loops including a plurality of elongated members curving in two opposite directions transverse to the circumferential direction. The elongated members are joined to one another at cusps pointing in opposed axial directions, the cusps being movable in the opposed axial directions between an expanded condition and a collapsed condition. In the expanded condition, the cusps pointing in one axial direction in at least one of the loops are spaced from the cusps pointing in the other axial direction in that loop by a predetermined distance and the elongated members define an expanded circumference. In the collapsed condition, the cusps pointing in the one axial direction in the loop are spaced from the cusps pointing in the other axial direction in the loop by a distance greater than the predetermined distance and the elongated members define a collapsed circumference smaller than the expanded circumference.

Another aspect of the present invention provides a method for forming an intraluminal stent. In accordance with the method, a plurality of forming members are provided, each having an axis extending in an orientation direction. Each of the forming members includes a curved surface extending parallel to the orientation direction, the surfaces being arranged in a predetermined position with respect to one another in an operative position of said members. A continuous filament may then be bent along the curved surfaces so as to form an intermediate member extending in an elongation direction transverse to the orientation direction. The intermediate member includes a plurality of elongated members curving in two opposite directions transverse to the elongation direction and a plurality of cusps interposed between the elongated members, the cusps pointing in directions transverse to the elongation direction. Each of the elongated members is curved over substantially the entire extent thereof between the cusps. The intermediate member may then be wound around a mandrel extending in a direction transverse to the elongation direction to form at least one loop having a preselected circumferential size.

BRIEF DESCRIPTION OF THE DRAWINGS

A more complete appreciation of the subject matter of the present invention and the various advantages thereof can be realized by reference to the following detailed description, in which reference is made to the accompanying drawings in which:

FIG. 5 is a perspective view of a high hoop strength stent including a plurality of the stents shown in FIG. 1 in stacked relationship;

FIG. 7A is a graph showing the hoop strength of a stent in accordance with the present invention as compared to the hoop strength of a prior art stent having a zig-zag configuration;

FIG. 7B is a highly schematic view of the test specimen configured in accordance with the present invention and used in the preparation of the graph of FIG. 7A;

FIG. 7C is a highly schematic view of the test specimen configured in accordance with the prior art and used in the preparation of the graph of FIG. 7A.

DESCRIPTION OF THE PREFERRED EMBODIMENTS

Figure 1:
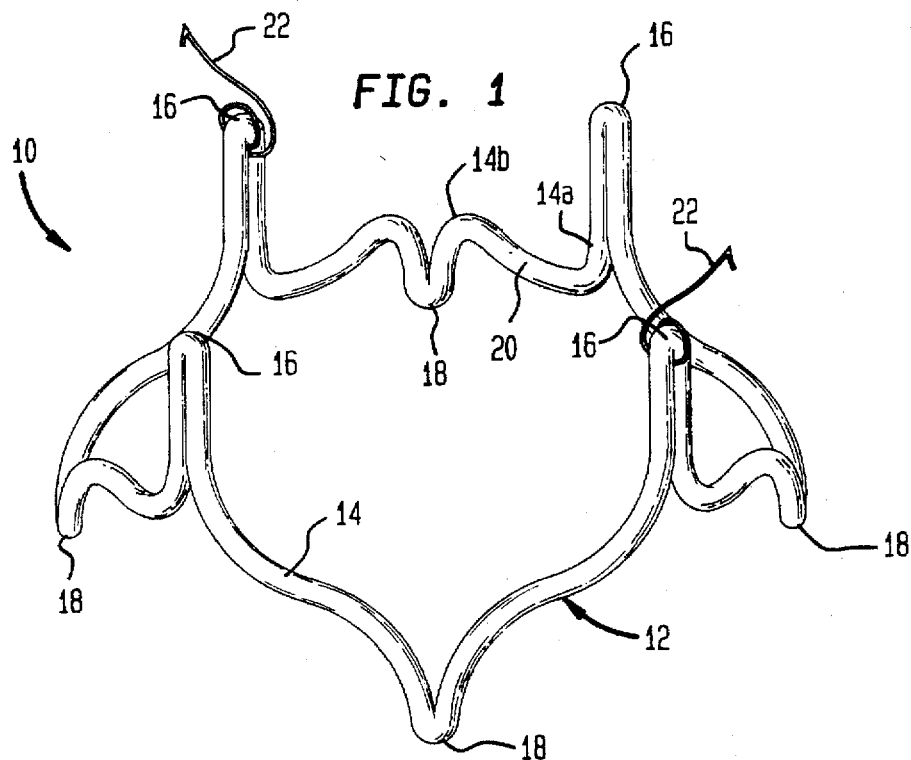
FIG. 1 is a perspective view of a high hoop strength stent in an expanded condition in accordance with one embodiment of the present invention.
Figure 2:
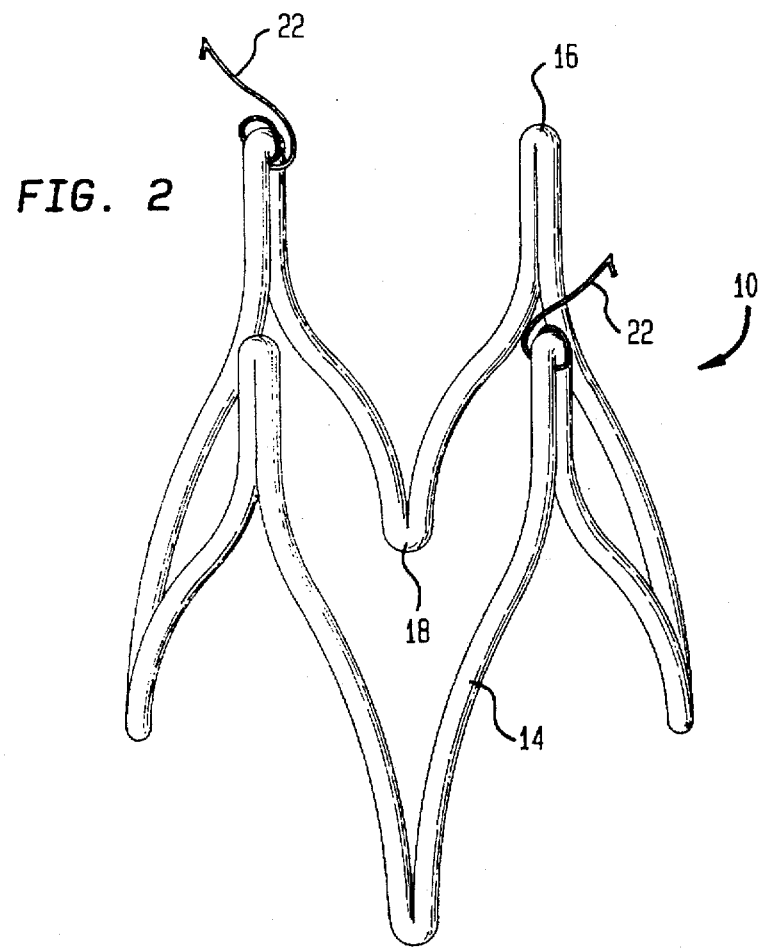
FIG. 2 is a perspective view of the stent of FIG. 1 in a partially contracted condition.
Figure 3:
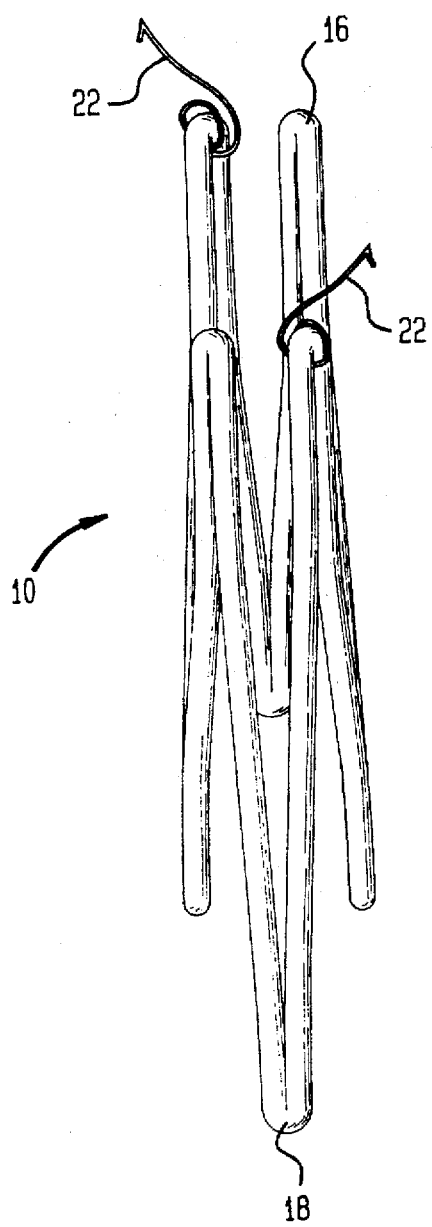
FIG. 3 is a perspective view of the stent of FIG. 1 in a fully contracted condition.

Referring to FIGS. 1–3, there is illustrated one preferred embodiment of a high hoop strength stent 10 in accordance with the present invention. Stent 10 may be formed from a filament 12 of a low shape-memory material. As used herein, the term "low shape-memory material" refers to materials that, once deformed from an initial shape to a subsequent shape, will tend to maintain the subsequent shape and not return to the initial shape. In this regard, filament 12 is preferably formed from a biologically-compatible metal. Such metals may include, for example, stainless steel, titanium, tantalum, gold, platinum, copper and the like, as well as alloys of these metals. Biologically-compatible low shape-memory plastics may also be used to form filament 12. Alternatively, filament 12 may be formed from a shape-memory plastic or alloy, such as nitinol, which automatically transforms from one shape to another shape as its temperature passes through a critical point.

Desirably, filament 12 comprises an elastic material; highly elastic materials being most preferred because of their tendency to return to their original shape following deformation. Whether filament 12 is formed from a low shape-memory material or from a shape-memory material is not critical, and impacts on the present invention predominantly in terms of the technique used to intraluminally deliver the stent to the repair site and fix same in place. In that regard, stents formed from low shape-memory materials are ordinarily delivered by a catheter to the repair site and expanded in a well-known manner by dilation of an angioplasty balloon, while stents formed from shape-memory alloys are normally thermally insulated in a catheter during delivery to the repair site and expand automatically upon passing through the critical temperature following deployment from the catheter.

Filament 12 may have a round cross-section as is typical of wires, or it may have a cross-section which is rectangular or another shape as desired. The size of the cross-section ordinarily will depend upon the particular application for which stent 10 is to be used. That is, for filaments having a round cross-section, the diameter of the filament may range from about 0.10 millimeters for stents used in the relatively small coronary arteries to about 0.50 millimeters for stents used in the much larger abdominal aorta. Moreover, the cross-section of the filament need not be constant along its entire length, but may include portions having a larger or smaller cross-section as desired. Filament 12 also need not be formed from a single continuous filament, but may consist of lengths of filament welded or otherwise joined together in end-to-end fashion.

FIG. 1 shows stent 10 in an expanded condition. Stent 10 includes a plurality of smoothly curved elongated members 14 which extend in a circumferential direction about a central axis. Elongated members 14 are joined to one another in end-to-end relationship at sharply bent cusps 16 and 18 which point in opposite axial directions so that members 14 together define an enclosed loop. Stent 10 may consist of discrete portions of filament 12 which are welded or otherwise joined together at cusps 16 and 18, respectively. Alternatively, stent 10 may be formed from a single continuous filament 12 bent into the configuration of elongated members 14 and cusps 16 and 18.

Figure 4:
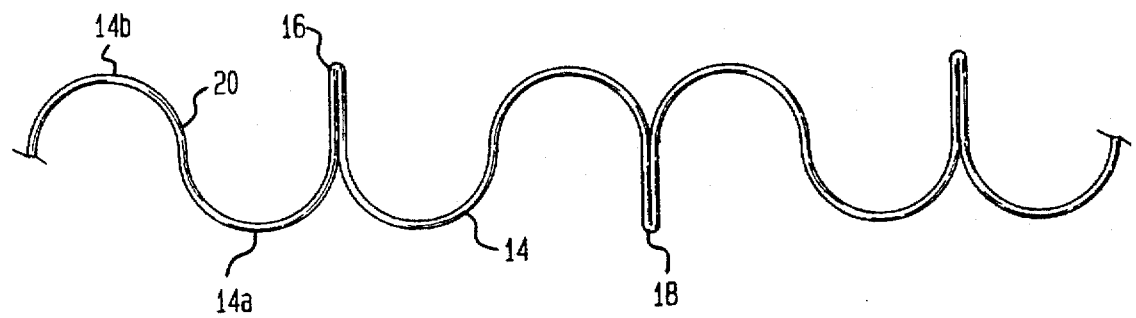
FIG. 4 is a highly schematic, partial elevational view of a high hoop strength stent in accordance with another embodiment of the present invention.

Each elongated member 14 is smoothly curved in opposite axial directions along substantially its entire length between adjacent cusps 16 and 18. That is, each elongated member 14 curves upwardly along a first portion 14a and downwardly along a second portion 14b, with the transition between the upwardly and downwardly curved portions occurring at a point of inflection 20. As explained above, by curving elongated members 14 along substantially their entire length, substantially all of filament 12 contributes to the hoop strength of stent 10. In this regard, the hoop strength of stent 10 in accordance with the present invention will be greater than the hoop strength of conventional stents regardless of the shape in which elongated members 14 are curved. However, the hoop strength of stent 10 in the expanded condition can be optimized by forming portions 14a and 14b of elongated members 14 with a constant radius of curvature so that these portions define arcs of a circle. For example, portions 14a and 14b may each define an arc described by an angle of about 90 degrees or one quarter of a circle, as shown in FIG. 1. Alternatively, elongated members 14 may be curved so that portions 14a and 14b each define an arc described by an angle of about 180 degrees or one half of a circle, as shown in FIG. 4, or by any angle greater than zero degrees. Elongated members in which curved portions 14a and 14b define an arc described by an angle of between about 30 degrees and about 180 degrees are most preferred.

Where it is to be used as a fixation device, stent 10 may be formed so that the cusps 16 pointing in one axial direction are longer than the cusps 18 pointing in the opposite axial direction. In this arrangement, the longer length of cusps 16 enables stent 10 to be placed inside an end portion of a prosthetic graft with cusps 16 protruding outwardly therefrom for fixation to the wall of a lumen. One or more of cusps 16 may then be provided with conventional barbs 22 which project outwardly in radial directions from stent 10. With stent 10 implanted within a lumen, barbs 22 penetrate the interior wall of the lumen to attach and hold the stent in place therein.

Because portions 14a and 14b of elongated members 14 are smoothly curved in opposite axial directions, a stent 10 formed from a highly elastic material can easily be folded from the expanded condition shown in FIG. 1 to the fully collapsed condition shown in FIG. 3 with little or no plastic deformation of filament 12. As used herein, the term "plastic deformation" refers to folding or bending filament 12 such that stent 10 will not return completely to its original expanded configuration. Accordingly, the ability to fold stent 10 from the expanded condition to the collapsed condition without plastic deformation means that stent 10 will return substantially to its original shape upon deployment. This is particularly true for shape-memory materials. Thus, as cusps 16 and 18 are pulled away from one another in opposite axial directions, the curved portions 14a and 14b of elongated members 14 will begin to straighten as shown in FIG. 2, and the circumference of stent 10 will decrease. Eventually, as cusps 16 and 18 continue to be pulled away from one another, stent 10 will reach the fully collapsed condition shown in FIG. 3 in which elongated members 14 are substantially straight and the circumference of the stent is at a minimum. Stent 10 may then be loaded into a catheter which holds the stent in this fully collapsed condition for intraluminal delivery and implantation within the body.

Where stent 10 is formed from a material which is not highly elastic and which therefore plasticly deforms upon folding from the expanded condition to the fully collapsed condition, returning the stent to its original expanded configuration may be more difficult. However, by altering the diameter of filament 12 along the length of elongated members 14, the amount of bending in the elongated members can be controlled to some extent so that the stent can be returned more closely to its original shape as it is radially expanded by balloon dilation.

Figure 8:
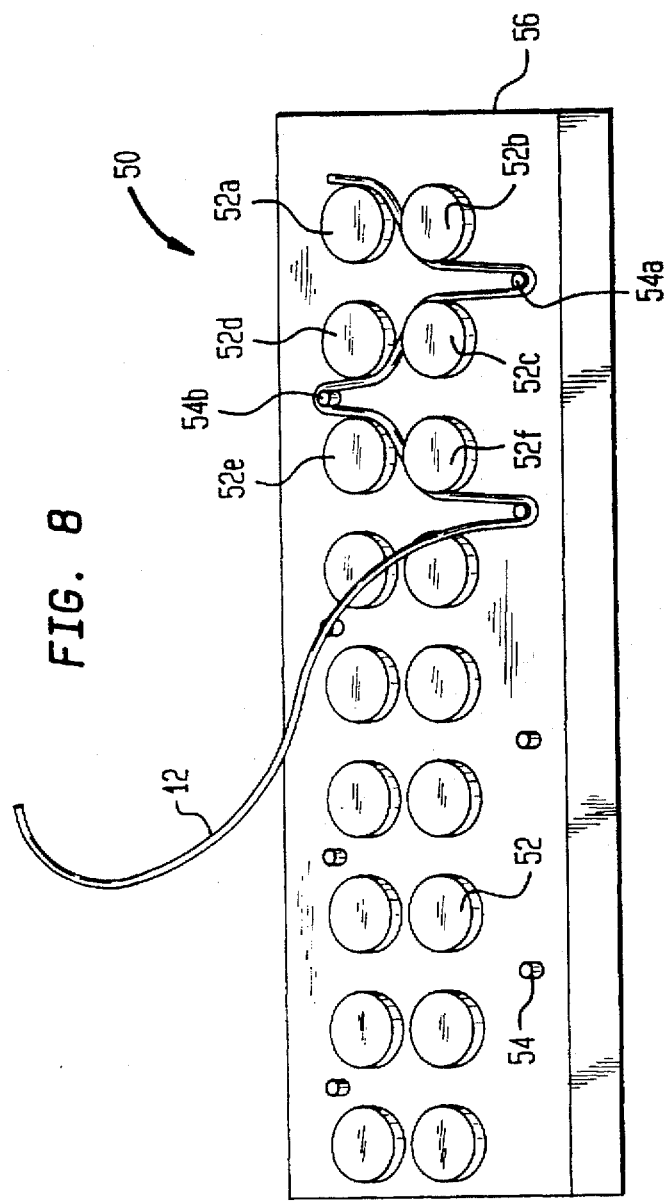
FIG. 8 is a perspective view of an apparatus for forming the stent in accordance with the present invention, showing a portion of a stent being formed thereon.

A preferred method for fabricating stent 10 can be understood with reference to FIG. 8. The method utilizes a form 50 consisting of a plurality of round pins 52 and 54 projecting from the top surface of a base 56. The shape of elongated members 14 and cusps 16 and 18 will be determined by the positions of pins 52 relative to one another and relative to pins 54. Thus, pins 52 and 54 in the form 50 illustrated in FIG. 8 are arranged so as to produce the stent shown in FIG. 1 in which elongated members 14 define arcs described by an angle of about 90 degrees and cusps 16 are longer than cusps 18. By changing the positions of pins 52 with respect to one another, elongated members defining arcs described by angles of between about zero and about 180 degrees can be formed. Furthermore, the lengths of cusps 16 and 18 can be altered by changing the positions of pins 54 relative to pins 52.

The shape and size of pins 52 and 54 will also influence the shape of elongated members 14 and cusps 16 and 18. That is, pins 54 are round and have a relatively small diameter, on the order of about 0.8 mm, so as to form the tight bends of cusps 16 and 18. The smaller the diameter of pins 54, the tighter the bends of these cusps will be. On the other hand, pins 52 have a relatively large diameter for forming the smoothly curved portions 14a and 14b of elongated members 14. Because pins 52 are round, portions 14a and 14b of elongated members 14 will have a constant radius of curvature. It will be appreciated that the diameter of pins 52 will determine the radius of curvature of portions 14a and 14b. For example, where a radius of curvature of about 3.0 mm is desired, pins 52 may have a diameter of about 6.0 mm. Where a larger radius of curvature is desired, pins 52 having a larger diameter may be used, and where a smaller radius of curvature in portions 14a and 14b is desired, smaller diameter pins 52 may be used. Although not necessary, all of pins 52 preferably will have about the same diameter so that the radius of curvature of all of the elongated members 14 in a stent will be about the same. Furthermore, pins 52 need not be round. Thus, to produce a stent in which elongated members 14 do not have a constant radius of curvature, pins 52 may include surfaces which are smoothly curved in shapes corresponding to the shapes to be reproduced in elongated members 14.

To produce a stent 10 using form 50, one end of a filament 12 may be inserted in the gap between pins 52a and 52b and the filament may then be fed downwardly therefrom along the surface of pin 52b toward and around pin 54a. As a result of the position of pin 54a with respect to pin 52b, filament 12 will contact pin 52b along approximately one quarter of its circumference, thereby producing a downward bend of about 90 degrees in filament 12. After passing around pin 54a, filament 12 may be directed upwardly until it contacts the surface of pin 52c. Filament 12 may then be fed along the surface of pin 52c until it reaches the gap between pins 52c and 52d, at which point it may be directed upwardly along the surface of pin 52d toward and around pin 54b, producing first a downward bend of about 90 degrees in filament 12 followed by an upward bend of about 90 degrees therein. After passing around pin 54b, filament 12 may be directed downwardly along the surface of pin 52e until it reaches the gap between pins 54e and 54f, resulting in another upward bend of about 90 degrees being formed in the filament. The foregoing steps of bending filament 12 along the surfaces of pins 52a–f and 54a–b will form one complete cycle of stent 10. A plurality of such cycles can be formed in series relationship by following this sequence of steps to feed filament 12 around the remainder of pins 52 and 54 on form 50. Hence, the number of cycles of stent 10 which can be formed on a single form 50 will depend upon the number of pins 52 and 54 arranged thereon. However, form 50 can be used to form an infinite number of continuous cycles merely by removing filament 12 therefrom after it has been bent around all of pins 52 and 54, shifting the filament to the right, and then reassembling the filament onto form 50 so that the leftmost cycle is in registry with the rightmost series of pins 52 and 54 on form 50. The remaining unbent portion of filament 12 can then be fed around the rest of pins 52 and 54 on form 50 and the process repeated to form a filament having any desired number of continuous cycles. In a variant of this process, a plurality of forms 50 can be juxtaposed in end-to-end relationship and filament 12 may then be fed in a continuous pattern from one of the forms to the next.

Once filament 12 has been fed around pins 52 and 54 to form the desired number of cycles of elongated members and cusps, the filament may be removed from form 50b in the form of a flat elongated structure, severed from any unbent portion of the filament which may remain, and trimmed to a preselected length. Where a stent having a minimum of bulk is desired, the portions of the elongated members on either side of each cusp may be crimped together to minimize the circumferential size of the stent in the collapsed condition. The flat structure may then be configured into a cylindrical loop by bringing the free ends thereof into opposed relationship and welding or otherwise joining same together. Since the flat structure has been formed or cut to a preselected length, the circumference of this loop will approximate the size desired in stent 10. The final sizing and shaping of stent 10 can then be accomplished by fitting the stent over a round mandrel having the desired circumferential size. A wire or foil wrap or a pair of opposed semi-circular members may be used to hold the stent tightly against the mandrel, and the entire assembly may then be placed inside an oven to anneal stent 10 and fix its final size and shape. Processes for annealing stent 10 are conventional in the art, and will depend upon the material from which stent 10 is formed.

A comparison of the hoop strength of a stent formed in accordance with the present invention relative to the hoop strength of a stent formed with a conventional zig-zag shape is shown in FIG. 7A. In this figure, the upper graph represents the hoop strength developed by two legs (one cycle) of a stent in accordance with the present invention (i.e. from a first cusp to a third cusp), in which the curved portions 14a and 14b each define a 90 degree arc as illustrated in FIG. 7B. The lower graph represents the hoop strength developed by the two legs on either side of a bend in a stent having a conventional zig-zag construction as illustrated in FIG. 7C. Both of the test specimens were formed from a wire having the same composition and diameter. The length of the wire used to form the test specimens was also the same. That is, the length of the filament between adjacent cusps in the test specimen shown in FIG. 7B was substantially the same as the length of the filament between adjacent bends in the test specimen shown in FIG. 7C.

In conducting the comparative test, both test specimens were initially configured to have an extension e of about 12 mm between the free ends of their legs when in a relaxed, expanded condition. The test specimens were then placed in a collapsed condition by bringing the free ends of the legs together (i.e., e=0 mm), and the force required to hold the legs in this fully collapsed condition was measured. This force was gradually reduced so that the free ends of the legs would expand away from one another and was measured at 1 mm increments of extension. As can be seen from the graph, the hoop strength of the stent constructed in accordance with the present invention is initially about 40% greater than the hoop strength of the stent having a conventional zig-zag construction. This difference in strength increased as the stents approached their initial extension. Thus, the specimen in accordance with the present invention still exhibited considerable hoop strength as it approached its original 12 mm extension. To the contrary, the hoop strength of the zig-zag specimen decreased much more rapidly and reached a value too low to be measured much sooner, indicating a significant amount of plastic deformation in the zig-zag stent as it was compressed from the expanded condition to the collapsed condition.

In accordance with another embodiment hereof, improved hoop strength may also be achieved in an elongated cylindrical stent for maintaining the patency of a body lumen or for supporting the entire extent of a prosthetic graft. As illustrated in FIG. 5, one such elongated stent 60 may include four stents in stacked relationship with the upwardly pointing cusps in one stent aligned with the downwardly pointing cusps in the stent immediately thereabove. Three of the stents, namely, stents 62, 64 and 66, may be substantially identical and include elongated members 67 defining arcs of about 90 degrees having a constant radius of curvature and upwardly pointing cusps 68 which are substantially the same length as downwardly pointing cusps 70. Of course, elongated members 67 may define arcs of between about 30 degrees and about 180 degrees as desired, and need not have a constant radius of curvature so long as elongated members 67 are smoothly curved over substantially their entire extent between cusps 68 and 70. An uppermost stent 72 is substantially the same as stents 62, 64 and 66, with the exception that its upwardly pointing cusps 74 are substantially longer than its downwardly pointing cusps 76. Barbs 78 may be connected to one or more of upwardly pointing cusps 74. Adjacent stents may be connected to one another by welding at least one opposed pair of cusps in each adjacent pair of stents together, as indicated generally at 80. Alternatively, adjacent stents may be connected to one another by suturing or otherwise tying together at least one pair of opposed cusps in each adjacent pair of stents. It will be appreciated that elongated stent 60 may include more or less than four stents in stacked relationship depending upon the overall length with which stent 60 is to be formed. Also, elongated stent 60 need not include a stent such as stent 72 in which the upwardly pointing cusps are substantially longer than the downwardly pointing cusps, and also need not include any barbs 78.

Figure 6:
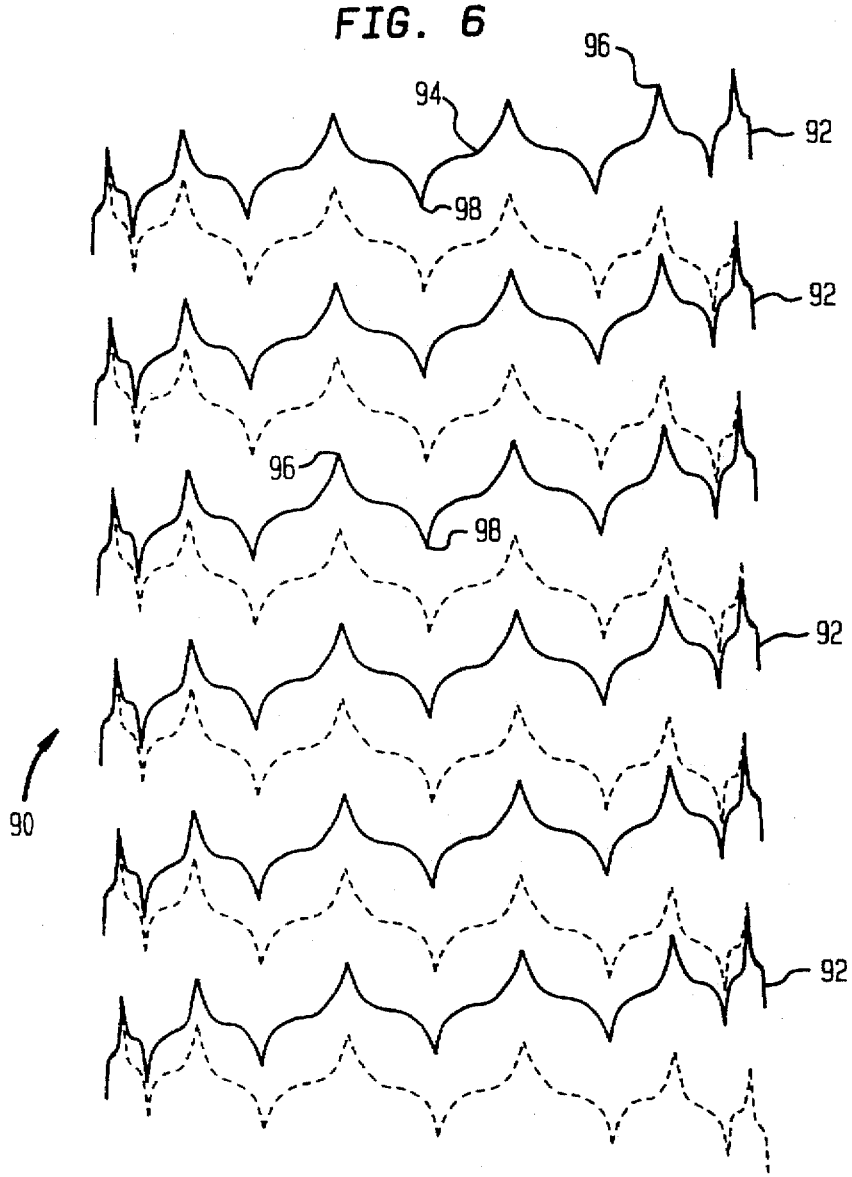
FIG. 6 is a highly schematic elevational view of a high hoop strength stent similar to that shown in FIG. 5 but including a plurality of helical convolutions.

Yet another embodiment of an elongated cylindrical stent for maintaining the patency of a body lumen or for supporting the entire extent of a prosthetic graft is shown in FIG. 6. In accordance with this embodiment, an elongated stent 90 includes a plurality of parallel convolutions 92 arranged helically in a cylindrical pattern. Each of convolutions 92 includes a plurality of elongated members 94 which are smoothly curved along substantially their entire extent between upwardly pointing cusps 96 and downwardly pointing cusps 98. Although stent 90 is depicted as having elongated members 94 defining arcs of about 90 degrees with a constant radius of curvature, it will be appreciated that the arcs of elongated members 94 may be different than 90 degrees, for example, elongated members 94 may define arcs of about 180 degrees such as shown in FIG. 4. Moreover, elongated members 94 need not have a constant radius of curvature so long as elongated members 94 are smoothly curved over substantially their entire extent between adjacent cusps.

A method for forming elongated stent 90 may be similar to that described above in connection with the fabrication of stent 10. Thus, an elongated filament may be wound around a plurality of pins projecting in a predetermined pattern from the top surface of a form to produce a flat elongated structure including a multiplicity of cycles of elongated members and cusps. This elongated structure may then be wound in a helical pattern around a mandrel with a sufficient number of convolutions to produce a stent having the desired length. A stent having the desired circumferential size can be produced by selecting a mandrel having an appropriate diameter. The stent may then be held tightly against the mandrel using a wire or foil wrap or a pair of opposed semi-circular members, and the entire assembly may be annealed in a conventional process to fix the final size and shape of the stent.

In the embodiments illustrated in FIGS. 5 and 6, the circumference of each circumferential loop or convolution of the illustrated stent is substantially the same. It will be appreciated, however, that this need not be the case and that the circumference of adjacent loops or convolutions can differ, such as by combining stents of different diameters for the embodiment in FIG. 5 or by using a shaped mandrel for the embodiment in FIG. 6, so as to form an elongated stent having a shape that is different from that of a right cylinder. For example, by altering the circumference of adjacent sections, stents having tapered or stepped profiles can be provided.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A method for forming an intraluminal stent, comprising the steps of:

providing a plurality of forming members each having an axis extending in an orientation direction, each said forming member including a curved surface extending parallel to said orientation direction, said surfaces being arranged in a predetermined position with respect to one another in an operative position of said forming members, bending a continuous filament along said curved surfaces so as to form an intermediate member extending in an elongation direction transverse to said orientation direction, said intermediate member including a plurality of elongated members curving in two opposite directions transverse to said elongation direction and a plurality of cusps interposed between said elongated members, said cusps pointing in directions transverse to said elongation direction, each said elongated member being curved over substantially its entire extent between said cusps, and curving said intermediate member to form at least one loop having a preselected circumferential size.

2. A method as claimed in claim 1, wherein said curving step includes the step of winding said intermediate member around a mandrel having said preselected circumferential size.

3. A method as claimed in claim 1, wherein said plurality of forming members include a first series of forming members having selected radii of curvature for forming said elongated members, and a second series of forming members having radii of curvature less than said selected radii of curvature for forming said plurality of cusps.

4. A method as claimed in claim 3, wherein said radius of curvature of each one of said first series of forming members is the same.

5. A method as claimed in claim 3, wherein said radius of curvature of each one of said second series of forming members is the same.

6. A method as claimed in claim 3, wherein said first series of forming members includes a first group of forming members aligned in a first row extending in said elongation direction and a second group of forming members aligned in a second row extending in said elongation direction, said bending step including the step of bending said filament along two adjacent ones of said forming members in said first group and then along two adjacent ones of said forming members in said second group.

7. A method as claimed in claim 6, wherein said bending step further comprises the step of bending said filament along one of said forming members in said second series between each two adjacent ones of said forming members in said first series.

8. A method as claimed in claim 1, further comprising the step of heating said at least one loop to an annealing temperature to fix said at least one loop at said preselected circumferential size.

* * * * *